United States Patent [19]

Fjare

[11] Patent Number: 4,952,721

[45] Date of Patent: Aug. 28, 1990

[54] PROCESS FOR OXIDIZING ESTERS OF METHYL-SUBSTITUTED PHENOL COMPOUNDS TO AROMATIC CARBOXYLIC ACIDS

[75] Inventor: Kristi A. Fjare, Naperville, Ill.

[73] Assignee: Amoco Corporation, Chicago, Ill.

[21] Appl. No.: 389,274

[22] Filed: Mar. 8, 1989

Related U.S. Application Data

[63] Continuation-in-part of Ser. No. 156,708, Feb. 17, 1988, abandoned, which is a continuation-in-part of Ser. No. 16,679, Feb. 19, 1987, abandoned.

[51] Int. Cl.$^5$ .................... C07C 51/215; C07C 67/39
[52] U.S. Cl. .................................... 560/131; 260/405; 260/410.5; 560/77; 562/416; 562/417; 562/421; 562/475; 562/480; 562/524
[58] Field of Search .................... 560/13, 77; 562/416, 562/417, 421, 480, 475, 524; 260/405, 410.5

[56] References Cited

U.S. PATENT DOCUMENTS 4,314,073  2/1982  Crooks ............................... 562/416

FOREIGN PATENT DOCUMENTS 50-35066  11/1975  Japan .

Primary Examiner—Werren B. Lone
Assistant Examiner—Vera C. Clarke
Attorney, Agent, or Firm—Gunar J. Blumberg; William H. Magidson; Ralph C. Medhurst

[57] ABSTRACT

A process is disclosed for the oxidation of esters of para- and meta-methyl-substituted phenols to the corresponding aromatic carboxylic acid in the presence of a promoter comprising an anhydride of a lower aliphatic carboxylic acid and a heavy metal catalyst with or without the presence of bromine. The resulting carboxylic acids are useful in liquid crystal polymers and polymers useful in engineering plastics.

20 Claims, No Drawings

PROCESS FOR OXIDIZING ESTERS OF METHYL-SUBSTITUTED PHENOL COMPOUNDS TO AROMATIC CARBOXYLIC ACIDS

This is a continuation-in-part application of Ser. No. 156,708, filed Feb. 17, 1988, now abandoned, which is a continuation-in-part application of Ser. No. 016,679, filed Feb. 19, 1987 and now abandoned.

BACKGROUND OF THE INVENTION

The present invention relates to liquid phase process for oxidizing an ester of a para- or meta-methyl-substituted phenol selected from the group consisting of p-cresol, m-cresol, 3,4-dimethylphenol, 3,5-dimethylphenol and 3,4,5-trimethylphenol to produce an aromatic carboxylic or polycarboxylic acid. These acids are useful in liquid crystal polymers and polymers useful in engineering plastics. More particularly, the invention relates to a liquid phase process for the production of p-acetoxybenzoic acid and acetate esters of other phenolic compounds in high yield.

p-Acetoxybenzoic acid, as the acetylated derivative of p-hydroxybenzoic acid, is an important monomer for production of liquid crystal polymers. The acetylation step is normally quantitative, after p-hydroxybenzoic acid has been purified, usually by crystallization to remove by-products formed in the preparation of the p-hydroxybenzoic acid. 4-Acetoxylphthalic anhydride, the acetoxylated derivative of 3,4-dimethylphenol, is useful in production of ester-imide polymers for engineering applications.

DESCRIPTION OF THE PRIOR ART

In the prior art, processes have been developed for production of p-acetoxybenzoic acid and 5-acetoxyisophthalic acid.

The conventional process for production of p-acetoxybenzoic acid, that which comprises reacting potassium phenoxide as a mixture of potassium phenoxide and phenol with carbon dioxide in a Kolbe-Schmidt reaction to form p-hydroxybenzoic acid which in turn is acetylated by reaction with acetic anhydride, has long been considered the most economical and practical. However, the process suffers from overall low yields and the coproduction of undesirable by-products in production of p-hydroxybenzoic acid. These undesirable aromatic by-products include salicylic acid, acetylsalicylic acid, phenylacetate, and 4-hydroxyisophthalic acid, among others. Unreacted phenol may also be present.

Early processes for the manufacture of p-hydroxybenzoic acid from potassium phenoxide suffered from the problems of long reaction time, as much as 60 hours, the difficulty of controlling the reaction temperature since the reaction is strongly exothermic and low yields. In processes described in G.B. Pat. No. 942,418, mention is made of various methods used to control temperature of the reaction as, for example, by carrying out the reaction in a suitable solvent. Various phenols were proposed as solvents as well as use of a fluidized-bed process, aluminum oxide or kaolin being used as the diluting agent. G.B. Pat. No. 942,418 disclosed a method to overcome these problems wherein potassium phenoxide was reacted with carbon dioxide under a pressure of 2 to 6 atmospheres gauge at a temperature of 180° C. to 210° C. and in the presence of a nonreactive gas, e.g., nitrogen, the nonreactive gas being continuously removed from the reaction vessel to be cooled and recycled. By varying the speed of circulation of the gas and the effectiveness of the cooler, the temperature of the reaction is controlled despite the exothermic course of the carbonization. Carbonization is complete after 5 to 10 hours.

U.S. Pat. No. 3,816,521 discloses a process for production of p-hydroxybenzoic acid from potassium phenoxide suitable for continuous operation wherein temperature is controlled by contacting potassium phenoxide which is suspended in a liquid hydrocarbon selected from the group consisting of kerosene, light oil and mixtures thereof which are boiling at 180° C.–350° C. with carbon dioxide pressurized not higher than 30 $kg/cm^2$ at temperatures not lower than 180° C. The reaction temperature is controlled by adjusting in advance the cooling temperature of the reaction mixture and the addition of up to 20 percent of water. Yield of p-hydroxybenzoic acid, based on potassium phenoxide, is disclosed as reaching 75 percent after a reaction time of one hour. Salicylic acid and 4-hydroxyisophthalic acid are disclosed in the examples as by-products.

The problems as noted above encountered in preparing p-hydroxybenzoic acid by the Kolbe-Schmidt reaction from a phenoxide salt and carbon dioxide, namely reaction temperature control and production of undesirable by-products have caused investigators to examine other methods of preparing p-hydroxybenzoic acid and the acylated derivative, p-acetoxybenzoic acid. Japanese Kokoku patent application Ser. No. SHO No. (1975)--35066 discloses a method for preparation of hydroxybenzoic acid and hydroxybenzaldehyde by oxidation of cresylacylate with molecular oxygen. The reaction is in the presence of organic acids and/or anhydrides as solvents, and a catalytic system comprising a ternary mixture of a bromine compound, a cobalt compound and a manganese compound. The organic acids and acid anhydrides exemplified in Table II are acetic acid and acetic anhydride. When anhydride is added to the reaction, all of it is added in the beginning of the reaction. The anhydride is not staged nor is it added during the course of the oxidation reaction. A large quantity of by-products are produced. Yields of acetoxybenzoic acid were 39.6%, 42.3% and 12.6%. Yields of acetoxybenzaldehyde, hydroxybenzaldehyde and hydroxybenzoic acid were a total of 24.9%, 13.4% and 7.8%. Residual feed materials were 37.5%, 42.1% and 55.8%. Undesirable product and unreacted materials accordingly totalled 62.4%, 55.5% and 63.6%, with the result that the process is inefficient and uneconomic and cannot be used in a competitive economy, yield of usable product being even less than obtained by other processes in prior art.

In the oxidation of p-cresylacetate, it is believed that it is generally impossible to avoid oxidation of the nuclei unless moderate process conditions are employed. However, even in such a case, small quantities of phenols can be produced during the reaction which inevitably inhibit the reaction. This is not unexpected, for phenols are known oxidation inhibitors, and phenols have also been found to decompose to carbon oxides readily under oxidation conditions.

The low yields obtained by previously disclosed processes for obtaining p-acetoxybenzoic acid and its precursor, p-hydroxybenzoic acid, as well as the concomitant production of undesirable by-products, necessitated the development of an improved process for preparation of p-acetoxybenzoic acid in a highly pure state.

Far superior results have been obtained by the process of the instant invention wherein yields of p-acetoxybenzoic acid of 95 percent have been obtained. Unreacted feed material is minimal.

Japanese Kokai Patent No. 51 [1976]-108030 discloses a method for preparation of 5-hydroxyisophthalic acid by oxidation of 5-acyloxy-m-xylene with molecular oxygen by using a heavy metal compound and a bromic compound as catalysts and in the presence of a low molecular weight aliphatic carboxylic acid and an acid anhydride followed by hydrolysis. The product is useful as a cross-linking agent in polymers. However, the product is not useful in ester-imide compounds.

Accordingly, it is an object of the present invention to provide a process for oxidizing esters of methyl-substituted phenols selected from the group consisting of p-cresol, m-cresol, 3,4-dimethylphenol and 3,4,5-trimethylphenol, the aromatic carboxylic or polycarboxylic acid products being useful in ester-imide polymers.

It is an object of the present invention to provide a process for the selective production of p-acetoxybenzoic acid from p-cresylacetate in high yield.

Another object of this invention is to provide a process for production of p-acetoxybenzoic acid in a very short time wherein the reaction conditions such as temperature are easily controlled.

Another object of this invention is to provide a process for production of m-acetoxybenzoic acid.

Another object of this invention is to provide a process for production of 4-acetoxyphthalic anhydride and acid, and other acetate esters of para- and meta-methyl-substituted phenols.

Another object of this invention is to provide a process for production of p- and m-acetoxybenzoic acids and acetoxy phthalic anhydride.

Another object of this invention is to provide a process for preparation of p- and m-acetoxybenzoic acids and acetoxy phthalic anhydride which enables the continuous or semicontinuous preparation of these compounds, thereby making economic mass production possible.

These and other objects and advantages of this invention will become apparent from the following descriptions.

SUMMARY OF THE INVENTION

A process is disclosed for oxidizing the esters and particularly the acetate esters of para- and meta-methyl-substituted phenols selected from the group consisting of p-cresol, m-cresol, 3,4-dimethylphenol, 3,5-dimethylphenol and 3,4,5-trimethylphenol to the corresponding aromatic carboxylic or polycarboxylic acid in high yield in the presence of a catalytic system and a promoter comprising an acid anhydride. The process can be batch, continuous or semicontinuous.

DETAILS OF THE INVENTION

The invented process for the oxidation of esters of para- and meta-methyl substituted phenols to their corresponding aromatic carboxylic or polycarboxylic acids, and specifically the process for preparation of p-acetoxybenzoic acid (pABA) from p-cresylacetate (pCA), m-acetoxybenzoic acid (mABA) from m-cresylacetate (mCA), or 4-acetoxyphthalic anhydride (4-APA) from 3,4-dimethylphenol (3,4-DMP) can be batch, continuous or semicontinuous. By semicontinuous is meant gradual addition of feedstock to the oxidation reactor. In commercial operation, continuous or semicontinuous process is preferred because it is easier to control reaction rates, temperature, pressure and other process parameters. In a continuous reaction, more product can be made in a given period. In this process the methyl groups on the phenol ester are oxidized in high yield to carboxylic acid groups.

Although the following discussion is devoted to the production of p-acetoxybenzoic acid, the discussion also applies to the preparation of the other above-mentioned carboxylic acids. The following discussion also applies to the oxidation of esters of the above-mentioned para- and meta-substituted phenols other than the acetate esters. For example, the esters made by reacting the hereinabove mentioned para- and meta-substituted phenols with a carboxylic acid, anhydride, acid halide or other reagent capable of transforming the phenol functionally into an ester functionality, are suitable esters for the invented process. The esters that have from 1 to 8 carbon atoms in the acid portion of the ester molecule are preferred. The acid portion may be aliphatic, aromatic, unsaturated, cyclic, mono, di-or polycarboxylic and may have other substituents as well. From the standpoints of economy and convenience, the more preferred esters are the esters of formic, acetic or propionic acid. The most preferred esters are the acetate esters, i.e. the esters of acetic acid. Also, if an ester other than an acetate ester is used in the process of this invention and acetic anhydride is used as a promoter, the aromatic carboxylic or polycarboxylic acid product isolated after the oxidation of the methyl groups to carboxylic acid groups may contain the phenol portion in the form of an acetate ester due to an ester crossover or exchange reaction. The isolated product may also be a mixture of esters, depending on the amount of acetic anhydride promoter used and the susceptibility of the initial ester employed to undergo an exchange reaction with the acetic anhydride promoter. Likewise, if an acetate ester of the methyl substituted phenol is used as the starting material and the anhydride of, for example, propionic acid is used as a promoter, the aromatic acid or aromatic polycarboxylic acid product will likely contain the phenol portion as the propionate ester or a mixture of acetate and propionate esters depending on the degree of ester exchange reaction that occurs.

In the production of p-acetoxybenzoic acid from p-cresylacetate (pCA), it has been discovered that the presence of acetic anhydride acts to promote the reaction. It has also been discovered that it is essential that the initial mole ratio of acetic anhydride to p-cresylacetate in the reaction be maintained within the range of from 1.0:1 to 1.58:1, and the total mole ratio in the range of 1.6:1 to 3.0:1. If the initial mole ratio of acetic anhydride to pCA is less than 1.0:1, the yield of pABA decreases significantly and the amount of impurities and by-products increases. Conversely, if the initial mole ratio of acetic anhydride to pCA is greater than about 1.58:1, the yield of pABA also decreases significantly. Accordingly, it has been discovered that it is essential to continually add acetic anhydride to the reaction to maintain the required level of acetic anhydride as promoter.

The unique effect of maintaining the continuous addition of acetic anhydride to the reaction can be understood from Table I. Run No. 94 had an initial charge of acetic anhydride only. Runs 164, 170, 174, 178, 138 and 140 had an initial charge to the reaction of acetic anhydride and added acetic anhydride during the course of the reaction. Runs 138 and 140 produced a low yield of p-acetoxybenzoic acid because initial charge of acetic anhydride was less than 1.0 mole % relative to p-cresylacetate.

TABLE I

| Run No. | Initial Moles Ac₂O to pCA | Total Moles Ac₂O to pCA | Product Moles pABA | Unreacted pCA Mole % |
|---|---|---|---|---|
| 94 | 2.94 | 2.94 | 48 | 11 |
| 164 | 1.02 | 1.47 | 66 | ND |
| 170 | 1.05 | 2.6 | 88 | ND |
| 174 | 1.05 | 1.64 | 84 | ND |
| 178 | 1.05 | 2.5 | 90 | ND |
| 138 | 0.74 | 1.47 | 35 | 22 |
| 140 | 0.74 | 1.43 | 48 | 10 |

Note:
pCA-p-cresylacetate
Ac₂O-Acetic anhydride
pABA-p-Acetoxybenzoic acid
ND-Not detected by gas chromatography or liquid chromatography analyses The metal oxidation catalyst components are cobalt and manganese, or cobalt, manganese and zirconium. Total metal concentration based on pCA is in the range of about $2.0 \times 10^{-3}$ to about $4.0 \times 10^{-2}$ moles per mole of pCA, preferably $3.0 \times 10^{-2}$ moles per mole of pCA, in combination with a source of bromine providing a bromine to metal ratio of about 0.4 to about 5.0, preferably about 0.7 to about 1.4, on a weight basis. The manganese component of the catalyst is in the range of about 45.0 to about 55.0 weight percent based on the total weight of the catalyst metals. The zirconium content of the total metals used is in the range of from about 1.0 to about 5.0, preferably about 1.5 to about 2.5 percent by weight of the total metals. The cobalt component of the catalyst is in the range of about 45 to about 55 weight percent of the total metals.

Although cobalt, manganese and zirconium used either alone or in any combination are the preferred metals for the catalyst of this invention, other heavy metals are also suitable. The heavy metals of interest here are those metals having an atomic number of not greater than 84. Nickel, cerium, hafnium, molybdenum, titanium, cobalt, magnesium and zirconium are the preferred heavy metals. These heavy metals may be used alone or in any combination, and with or without the presence of bromine or a bromine compound.

The solvent for the reaction is a lower carboxylic acid which can be acetic acid or propionic acid. Acetic acid is preferred with the promoter of acetic anhydride. The promoter can be propionic anhydride in which case propionic acid is preferred as solvent. However, it is not essential for the promoter anhydride and solvent to be derived from the same lower carboxylic acid.

The source of molecular oxygen can be air or any other source of oxygen which is economic and convenient. Air is preferred because of economics and ease of handling.

When the oxidation of pCA is conducted batchwise with acetic acid as solvent and acetic anhydride as promoter, the acid and anhydride are premixed in a separate vessel. The ratio of acid to anhydride is in the range of from about 4.0:1 moles to 5.0:1 moles, acid to anhydride, preferably 4.25:1 moles. The mixture is then added to pCA wherein the ratio of anhydride to pCA is about 1.05 moles anhydride to 1 mole pCA. Catalysts comprising cobalt, manganese, zirconium and bromine are added to the reactor.

The total bromine added can be from a single source of bromine, for example, ionic bromine sources (HBr, NaBr, NH₄Br and the like) or from a combined form of bromine, for example, organic bromides such as benzyl bromide, tetrabromoethane and others.

This novel process relates to the liquid-phase oxidation of pCA to pABA using cobalt, manganese and/or other heavy metals, such as zirconium plus bromine. A useful catalyst for our process is a zirconium-cobalt-manganese-bromine catalyst wherein the molecular ratio of zirconium to cobalt is about 1 to about 10 to about 1 to about 40 and the oxidation is conducted at a temperature in the range of about 200° F. to about 350° F., which process comprises conducting a batch oxidation of the pCA so that the concentration of bromine is 1.28:1 by weight.

In a specific embodiment, all components, except for all of the anhydride promoter, are charged to the reactor at or near oxidation initiation temperature, preferably at about 300° F. to about 350° F. and at a pressure to maintain liquid-phase conditions. Then, pressurized air is injected into the reaction mixture and the reaction temperature is permitted to increase by heat evolved by the oxidation reaction but kept below 400° F.

In one preferred embodiment of our process for the oxidation of pCA with molecular oxygen to pABA under liquid-phase conditions in the presence of a zirconium-cobalt-manganese-bromine catalyst, the molecular ratio of zirconium to cobalt is about 1:10 to about 1:40 and the temperature is in the range of about 100° C. to about 220° C.

This novel process also relates to the liquid-phase oxidation of pCA wherein the catalyst mixture essentially comprises cobalt, manganese and bromine, to the exclusion of zirconium. The exclusion of zirconium reduces the activity of the catalyst mixture slightly by reducing combustion of the feedstock to carbon dioxide. Choice and decision as to use of zirconium-containing catalyst mixtures will be subject to the economics of the two alternative procedures.

In the novel process, the initial mole ratio of acetic anhydride to the initial mole ratio of p-cresylacetate has been found to determine the amount of by-products produced. Preferably, the initial mole ratio of acetic anhydride to moles of pCA is in the range of from about 1.0 to about 2.94. If the initial mole ratio of anhydride is less than about 1.0:1.0, it has been found that large amounts of by-products are produced.

In a semicontinuous or continuous process, reactor effluent is evaporated to remove acetic anhydride and acetic acid. Recovered acetic acid from reactor effluent is recycled to the make-up vessel of acetic anhydride and acetic acid. The bottoms from the evaporator, containing the reactor product, are filtered to remove acetic anhydride, acetic acid and catalyst in the mother liquor. The mother liquor is then recycled. The filter cake can be recrystallized to improve purity from a suitable solvent which can be water, acetic acid, or an aromatic hydrocarbon.

The p-cresylacetate can be prepared by acylating p-cresol with acetic anhydride prior to the oxidation of the p-cresylacetate.

Preferably hydrogen bromide is used. Aqueous hydrogen bromide is preferable as the source of bromine because of ease of handling and safety. The unique effect of using HBr can be understood from Table II below. The reactions were run under comparable reaction conditions.

TABLE II

| Run No. | Bromine Source | Mole % pABA Yield |
|---|---|---|
| 111 | NaBr | 69 |
| 170 | HBr | 88 |
| 178 | HBr | 90 |

Table II shows the results of the reaction using sodium bromide and hydrogen bromide. Yield of product is from 10 percent to 20 percent mole percent greater with hydrogen bromide than with sodium bromide.

The instant invented process accordingly is a liquid phase process for production of p-acetoxybenzoic acid in high yield which process comprises: (a) oxidation of p-cresylacetate with a source of molecular oxygen in the presence of a catalyst, in a solvent comprising a lower aliphatic carboxylic acid and in the presence of a promoter consisting essentially of an acid anhydride of a lower aliphatic carboxylic acid, at a temperature within the range of from about 200° F. to about 400° F., and at a pressure of from 1 atmosphere to about 30 atmospheres, and (b) said promoter is present as an initial reactor charge in a mole ratio to said p-cresylacetate of at least 1.0:1 but less than 2.9:1, and (c) said promoter is added to said reactor charge during said oxidation in an amount of from 0.5:1 to 1.6:1 moles per mole of p-cresylacetate wherein total of said initial charge plus addition of said promoter is from about 1.5:1 to 3.0:1 moles promoter to p-cresylacetate.

The said catalyst can comprise a heavy metal compound, with or without the presence of a bromine compound. Preferably said heavy metal comprises one or more metals selected from the group consisting of cobalt, manganese, zirconium, nickel, cerium, hafnium, molybdenum and titanium. More preferably, said catalyst comprises a cobalt (II) compound, a manganese (II) compound and a bromine compound. Also more preferred is a catalyst comprising a cobalt (II) compound and/or a manganese (II) compound, a zirconium compound and a bromine compound.

The metal concentration of total catalyst components, is in the range of from about $2.0 \times 10^{-2}$ to about $4.0 \times 10^{-2}$ moles per g mole of p-cresylacetate, in combination with a source of bromine providing a bromine to metal ratio of about 0.4 to about 5.0 upon a weight basis. The zirconium content of total metals of said catalyst is in the range of from about 0 to about 5.0 weight percent of the total metals, the manganese content is in the range of from about 45 to 55 weight percent of the total metals and cobalt content is in the range of from about 45 to 55 weight percent of the total metals. The source of molecular oxygen can comprise air. The process can be a batch process, or a semicontinuous process, or a continuous process.

In summary, the instant invention comprises a liquid-phase process for the oxidation of an ester of a para- or meta-methyl-substituted phenol selected from the group consisting of p-cresol, m-cresol, 3,4-dimethylphenol, 3,5-dimethylphenol and 3,4,5-trimethylphenol to an aromatic carboxylic or polycarboxylic acid in high yield which process comprises: (a) oxidation of said ester with a source of molecular oxygen in the presence of a catalyst comprising one or more heavy metals, in a solvent comprising a lower aliphatic carboxylic acid and in the presence of a promoter consisting essentially of an acid anhydride of a lower aliphatic carboxylic acid, at a temperature within the range of from about 275° F. to about 400° F., and at a pressure of from 1.0 atmospheres to about 30 atmospheres, and (b) said promoter is present as an initial reactor charge in a mole ratio to said ester of at least 1.0:1, but less than 2.9:1, and (c) said promoter is added to said reactor charge during said oxidation in an amount of from 0.5:1 to 1.6:1 moles per mole of said ester wherein total of said initial charge plus addition of said promoter is from about 1.5:1 to 3.0:1 moles promoter to said esters. Preferably said catalyst, with or without the presence of bromine or a bromine compound, is one or more heavy metals selected from the group consisting of cobalt, manganese, zirconium, nickel, cerium, hafnium, molybdenum and titanium. Preferably said ester contains from 1 to 8 carbon atoms in the acid portion of the ester molecule. Most preferably said ester is an acetate ester.

More preferably said catalyst comprises a cobalt (II) compound, a manganese (II) compound, and a bromine compound, or a cobalt (II) compound, a manganese (II) compound, a zirconium compound, and a bromine compound. The metal concentration of total catalyst components can be in the range of from about $2.0 \times 10^{-3}$ to about $4.0 \times 10^{-2}$ moles per g mole of p-cresylacetate, in combination with a source of bromine providing a bromine to metal ratio of about 0.4 to about 5.0, upon a weight basis. The zirconium content of total metals of said preferred catalyst is in the range of from about 0 to about 5.0 weight percent of the total metals, the manganese content is in the range of from about 45 to 55 weight percent of the total metals and cobalt content is in the range of from about 45 to 55 weight percent of the total metals. The source of molecular oxygen can comprise air. The invented process can be a batch process, or a semicontinuous process, or a continuous process. The said lower aliphatic carboxylic acid solvent is preferably selected from the group consisting of acetic acid and propionic acid. The said promoter preferably is selected from the group consisting of acetic anhydride and propionic anhydride. The said lower aliphatic carboxylic acid is more preferably acetic acid and said promoter is acetic anhydride. The process conditions most preferably comprise a reaction temperature within the range of from about 275° F. to 375° F., a pressure of from about 1 atmosphere to about 30 atmospheres more preferably from about 2 to about 30 atmospheres and most preferably from about 10 to about 30 atmospheres, and said source of molecular oxygen is air.

The novel process is exemplified by the following examples. These examples are exemplary only and are not meant to be construed as limiting. Examples I and II exemplify the process wherein the reaction was run at atmospheric pressure and 100° C. The reaction times were 71 hours and 75, respectively. Examples I and II accordingly illustrate the exceedingly long reaction time required by atmospheric pressure and a temperature of 100° C.

EXAMPLE I

Twenty (20) g. (0.13 moles) of p-cresylacetate, 40 g. (0.39 moles) of acetic anhydride, 40 g. (0.67 moles) of acetic acid, 0.5 g. (0.002 moles) Co(OAc)$_2$·4H$_2$O, 0.49 g. (0.002 moles) Mn(OAc)$_2$·4H$_2$O, and 0.43 g. (0.004 moles) NaBr were combined in a glass reactor and heated to 100° C. at atmospheric pressure under air flow of 50 ml/min. The reaction was continued for 71 hours at which time oxygen uptake ceased. Upon cooling, the reaction mixture solidified. Analysis of this material showed p-acetoxybenzoic acid in 77 mole percent yield and p-acetoxybenzaldehyde in 5 mole percent yield. No unreacted p-cresylacetate was detected. The low yield is believed to result from work-up procedures.

EXAMPLE II

Fourteen and 6/10 (14.6) g. (0.135 moles) p-cresol and 16.3 g. (0.160 moles) acetic anhydride were combined in a glass reactor and heated to 100° C. under nitrogen flow for 2 hours to prepare p-cresylacetate. This solution was cooled and 40 g. (0.67 moles) of acetic acid, 38.2 g. (0.374 moles) of acetic anhydride, 0.5 g. (0.002 moles) $Co(OAc)_2 \cdot 4H_2O$, 0.49 g. (0.002 moles) $Mn(OAc)_2 \cdot 4H_2O$, and 0.43 g. (0.004 moles) of NaBr were added. The mixture was heated to 100° C. under air flow as described in Example I. Oxidation continued for 75 hours. Analysis of the reaction mixture showed a 95 mole percent yield of p-acetoxybenzoic acid, 2 mole percent yield of p-acetoxybenzaldehyde and 0.3 mole percent of p-hydroxybenzoic acid. There was no evidence of unreacted p-cresylacetate.

EXAMPLE III

Twenty (20) g. (0.13 moles) of m-cresylacetate was combined with acetic acid, acetic anhydride and catalyst as described in Example I. The oxidation continued for 74 hours. Analysis of the reaction mixture showed 1 mole percent yield unreacted m-cresylacetate. The reaction mixture was dried to a solid, combined with excess 0.1N aqueous NaOH and refluxed until the pH of the solution was no longer acidic. The solution was cooled and reacidified with dilute HCl. Analysis of the reaction solution showed m-hydroxybenzoic acid, 83 mole percent yield, m-hydroxybenzaldehyde, 4 mole percent yield, and unreacted m-cresylacetate 1 mole percent.

EXAMPLE IV

One hundred and forty (140) g. (0.932 moles) p-cresylacetate, 250 g. (4.16 moles) acetic acid, 100 g. (0.98 moles) acetic anhydride, 3.5 g. (0.014 moles) $Co(OAc)_2 \cdot 4H_2O$, 3.5 g. (0.014 moles) $Mn(OAc)_2 \cdot 4H_2O$, and 4.7 g. (0.028 moles) 48 percent HBr were combined in a two-liter titanium-clad autoclave. The reaction was heated to 300° F. and 300 psi pressure. Air was introduced at a rate of 0.78 scf/min. During the oxidation a solution of 138 g. (1.35 moles) acetic anhydride and 35 g. (0.58 moles) acetic acid was added through a pump. The oxidation ceased after 23 minutes. Analysis of the total reactor effluent and wash showed p-acetoxybenzoic acid, 90 mole percent, p-acetoxybenzaldehyde, 0.5 mole percent, and p-hydroxybenzoic acid, 1.3 mole percent. No unreacted p-cresylacetate was detected by analysis.

EXAMPLE V

One hundred and forty (140) g. (0.932 moles) of m-cresylacetate was oxidized as described in Example IV, in a two-liter titanium-clad autoclave, except that 160 g. (1.57 moles) of acetic anhydride and 40 g. (0.67 moles) of acetic acid were pumped in during the reaction. The reaction time was 25 minutes. Analysis of the total reactor effluent and wash showed 1.5 mole percent yield of m-hydroxybenzoic acid, with the remainder of the material being esterified products. Hydrolysis of the dried reaction mixture as described in Example IV gave m-hydroxybenzoic acid, 84 mole percent, and m-hydroxybenzaldehyde, 0.2 mole percent. No unreacted m-cresylacetate or m-cresol was detected by analysis.

EXAMPLE VI

The following example illustrates that the instant invented process is specific to para-and meta-compounds and is unsuitable for ortho-compounds.

One hundred and forty (140) g. (0.932 moles) o-cresylacetate, 250 g. acetic acid, 100 g. acetic anhydride, 3.5 g. (0.014 moles) $Co(OAc)_2 \cdot 4H_2O$, 3.5 g. (0.014 moles) $Mn(OAc)_2 \cdot 4H_2O$ and 4.7 g. (0.028 moles) 48 percent HBr were combined in a two-liter titanium-clad autoclave. The reaction mixture was heated to 300° F. and 300 psi pressure. Air was introduced at a rate of 0.78 scf/min. During the oxidation a solution of 132 g. (1.29 moles) acetic anhydride and 33 g. (0.55 moles) acetic acid was added through a pump. The oxidation ceased after 21 minutes. Analysis of the total reactor effluent and wash showed acetylsalicylic acid 0.8% yield, acetyl salicylaldehyde 0.6% yield, acetylsalicylacetate 3.4%, unreacted o-cresylacetate 79% yield. Unidentified black material constituted the remainder.

The experiment was repeated with the same result.

EXAMPLE VII

The following example illustrates the low yield obtained of product, 48 mole percent, when all acetic anhydride is added at the beginning of the reaction and none during the reaction period.

One hundred and forty (140) g. (0.932 moles) p-cresylacetate, 260 g. (4.33 moles) acetic acid, 280 g. (2.74 moles) acetic anhydride, 1.0 g. (0.004 moles) $Co(OAc)_2 \cdot 4H_2O$, 1.0 g. (0.004 moles) $Mn(OAc)_2 \cdot 4H_2O$, 0.8 g. (0.008 moles) NaBr were combined in a two-liter titaniumclad autoclave. The reaction mixture was heated to 300° F. and pressurized to 300 psi. Air was introduced at a rate of 0.78 scf/min. Oxidation ceased after 75 minutes. The reaction yields were: p-acetoxybenzoic acid, 48 mole percent, p-hydroxybenzoic acid, 0.1 mole percent, p-acetoxybenzaldehyde, 3.2 mole percent, unreacted p-cresylacetate, 11 mole percent.

EXAMPLE VIII

The following example illustrates the yield obtained by adding acetic anhydride to the process in a mole ratio of less than 1:1 to about 0.7:1, acetic anhydride to p-cresylacetate, at the beginning of the process, followed by an additional amount of acetic anhydride during the reaction in an amount to a final mole ratio of 1.96 to 1.33, acetic anhydride to p-cresylacetate.

Two hundred (200) g. (1.33 moles) p-cresylacetate, 140 g. (2.33 moles) acetic acid, 100 g. (0.980 moles) acetic anhydride, 5.0 g. (0.02 moles) $Co(OAc)_2 \cdot 4H_2O$, 4.9 g. (0.02 moles) $Mn(OAc)_2 \cdot 4H_2O$, and 4.13 g. (0.04 moles) NaBr were combined in a two-liter titanium-clad autoclave. The vessel was heated to 300° F. and pressurized to 300 psi. Air was introduced at a rate of 0.78 scf/min. During the reaction a solution of 100 g. (0.980 moles) acetic anhydride and 100 g. (1.67 moles) acetic acid was added though a pump. The oxidation ceased after 23 minutes. Reaction yields were: p-acetoxybenzoic acid, 35 mole percent, p-hydroxybenzoic acid, 1.6 mole percent, p-acetoxybenzaldehyde, 9.8 mole percent, p-hydroxybenzaldehyde, 0.7 mole percent, unreacted p-cresylacetate, 22 mole percent.

EXAMPLE IX

The following example illustrates the preparation of 4-acetoxyphthalic anhydride and acid wherein 1.47 moles of acetic anhydride were added to prepare the acetate from 0.934 moles of 3,4-dimethylphenol. An additional 0.49 moles of acetic anhydride were added prior to the oxidation reaction for a reaction amount of 1.026 moles of acetic anhydride, in a mole ratio of 1.1 to 1, acetic anhydride to the acetoxylated 3,4-dimethylphenol. An additional 1.96 moles of acetic anhydride were added during the oxidation for a total mole ratio of 3.2 to 1. Total amount of acetic anhydride accordingly is dependent upon the number of methyl groups in the starting compound.

One hundred and fourteen (114) g. (0.934 moles) of 3,4-dimethylphenol and 150 g. (1.47 moles) of acetic anhydride were combined in a two-liter titanium-clad autoclave and heated to 200° F. at 100 psi pressure under a nitrogen flow for one hour. The solution was cooled and 400 g. (6.66 moles) acetic acid, 50 g. (0.49 moles) acetic anhydride, 4.7 g. (0.028 moles) 48 percent HBr, 3.5 g. (0.014 moles) $Co(OAc)_2 \cdot 4H_2O$, and 3.5 g. (0.014 moles) $Mn(OAc)_2 \cdot 4H_2O$ were added. The mixture was heated to 320° F. (160° C.) and pressurized to 150 psi. During the course of the oxidation the reaction temperature was increased to 369° F. and pressure increased to 295 psi. Two hundred (200) g. (1.96 moles) of acetic anhydride was added during the oxidation through a pump. The run time was 30 minutes. Analysis of the reaction solution showed 60 mole percent yield of 4-acetoxyphthalic anhydride. Substantial amounts of the reaction intermediates 3- and 4-acetoxyphthalide (~10% total) and 3- and 4-acetoxy-2-carboxybenzaldehyde (~10% total) were also observed. Hydrolysis would permit preparation of the acid from the anhydride.

EXAMPLE X

The following example illustrates the poor yield obtained with addition of amounts of acetic anhydride to a final mole ratio of 4.98, an amount greater than a mole of about 3:1, over the course of the reaction.

Twenty g. (0.164 moles) 3,4-dimethylphenol dissolved in 40 g. (0.67 moles) acetic acid were added slowly to a mixture of 50 g. (0.49 moles) acetic anhydride and 0.34 g. (0.002 moles) 48 percent HBr in a glass reactor. The mixture was kept under nitrogen. It was heated to 100° C. for one hour. After this time 0.5 g. (0.002 moles) $Co(OAc)_2 \cdot 4H_2O$ and 0.49 g. (0.002 moles) $Mn(OAc)_2 \cdot 4H_2O$ were added and air introduced into the reactor at a rate of 50 ml/min. An additional 50 g. (0.49 moles) of acetic anhydride was added after one hour of oxidation. The reaction temperature was increased to 112° C. after 15.5 hours of oxidation. The reaction stopped after 63.5 hours. Analysis of the reaction mixture showed 4-acetoxyphthalic anhydride, 4.8 mole percent yield, and unreacted 3,4-dimethylphenylacetate, 1.4 mole percent yield.

What is claimed is:

1. A liquid-phase process for oxidation of an ester of a para- or meta-methyl-substituted phenol selected from the group consisting of a p-cresol, m-cresol, 3,4-dimethylphenol, 3,5-dimethylphenol and 3,4,5-trimethylphenol to oxidize the methyl groups on the phenol ester to carboxylic acid groups thereby converting the phenol ester to the corresponding aromatic carboxylic or polycarboxylic acid which process comprises:

(a) oxidation of said ester with a source of molecular oxygen comprising air in the presence of a catalyst comprising heavy metals selected from the group consisting of cobalt and manganese, and cobalt, manganese and zirconium, in a solvent comprising a lower aliphatic carboxylic acid selected from the group consisting of acetic acid and propionic acid and in the presence of a promoter consisting essentially of an acid anhydride of a lower aliphatic carboxylic acid selected from the group consisting of acetic anhydride and propionic anhydride, at a temperature within the range of from about 200° F. to about 400° F., and at a pressure of from about 1.0 atmospheres to about 30 atmospheres, and (b) said promoter is present as an initial reactor charge in a mole ratio to said ester of at least 1.0:1 but less than 2.9:1, and (c) said promoter is added to said reactor charge during said oxidation in an amount of from 0.5:1 to 1.6:1 moles per mole of said ester wherein total of said initial charge plus addition of said promoter is from about 1.5:1 to 3.0:1 moles promoter to said ester.

2. The process of claim 1 wherein said ester is the acetate ester of a para- or meta-methyl-substituted phenol selected from the group consisting of p-cresol, m-cresol, 3,4-dimethylphenol, 3,5-dimethylphenol and 3,4,5-trimethylphenol.

3. The process of claim 1 wherein the acid portion of said ester contains from 1 to 8 carbon atoms.

4. The process of claim 1 wherein said ester is para-cresyl-acetate.

5. The process of claim 1 wherein said catalyst further comprises a bromine compound.

6. The process of claim 1 wherein said catalyst comprises a cobalt(II) compound, a manganese(II) compound, and further comprises a bromine compound.

7. The process of claim 1 wherein said catalyst comprises a cobalt(II) compound, a manganese(II) compound, a zirconium compound, and further, comprises a bromine compound.

8. The process of claim 6 wherein said ester is para-cresyl-acetate.

9. The process of claim 7 wherein said ester is para-cresyl-acetate.

10. The process of claim 1 wherein the total concentration of said heavy metals in said catalyst is in the range of from about $2.0 \times 10^{-3}$ to about $4.0 \times 10^{-2}$ moles per g mole of said ester of said para- and meta-methyl-substituted phenols, said catalyst further comprising a source of bromine providing a bromine to metal ratio of about 0.4 to about 5.0, upon a weight basis.

11. The process of claim 7 wherein the zirconium content of total metals of said catalyst is in the range of from about 0 to about 5.0 weight percent of the total metals, the manganese content is in the range of from about 45 to 55 weight percent of the total metals and cobalt content is in the range of from about 45 to 55 weight percent of the total metals.

12. The process of claim 1 wherein said process is a batch process.

13. The process of claim 1 wherein said process is a semicontinuous process.

14. The process of claim 1 wherein said process is a continuous process.

15. The process of claim 1 wherein said lower aliphatic carboxylic acid is selected from the group consisting of acetic acid and propionic acid.

16. The process of claim 1 wherein said promoter is selected from the group consisting of acetic anhydride and propionic anhydride.

17. The process of claim 1 wherein said lower aliphatic carboxylic acid is acetic acid and said promoter is acetic anhydride.

18. The process of claim 1 wherein said process conditions comprise a reaction temperature within the range of from about 275° F. to 375° F., a pressure of from about 10 atmospheres to about 30 atmospheres and said source of molecular oxygen is air.

19. The process of claim 8 wherein said promoter is acetic anhydride.

20. The process of claim 9 wherein said promoter is acetic anhydride.

* * * * *